United States Patent [19]

Chen

[11] Patent Number: 5,356,395
[45] Date of Patent: Oct. 18, 1994

[54] SAFETY SYRINGE SHIELD

[76] Inventor: Shih-Shuan Chen, c/o Hung Hsing Patent Service Center, P.O. Box 55-1670, Taipei (104), Taiwan

[21] Appl. No.: 165,837
[22] Filed: Dec. 14, 1993
[51] Int. Cl.⁵ .............................................. A61M 5/00
[52] U.S. Cl. .................................... 604/263; 604/192
[58] Field of Search .............. 604/192, 198, 263, 187

[56] References Cited

U.S. PATENT DOCUMENTS 5,074,848 12/1991 Burt et al. ..................... 604/192 X
5,092,461 3/1992 Adam ............................. 604/263 X Primary Examiner—John D. Yasko

[57] ABSTRACT

A safety syringe shield includes an elongated closed cap for sealing a syringe needle threin and a cap holder secured to the elongated cap having a pair of holding guide members disposed on two opposite sides of the cap holder for holding the syringe shield to allow the syringe needle to be inserted into the elongated closed cap to prevent accidental contact of the user with the needle.

3 Claims, 3 Drawing Sheets

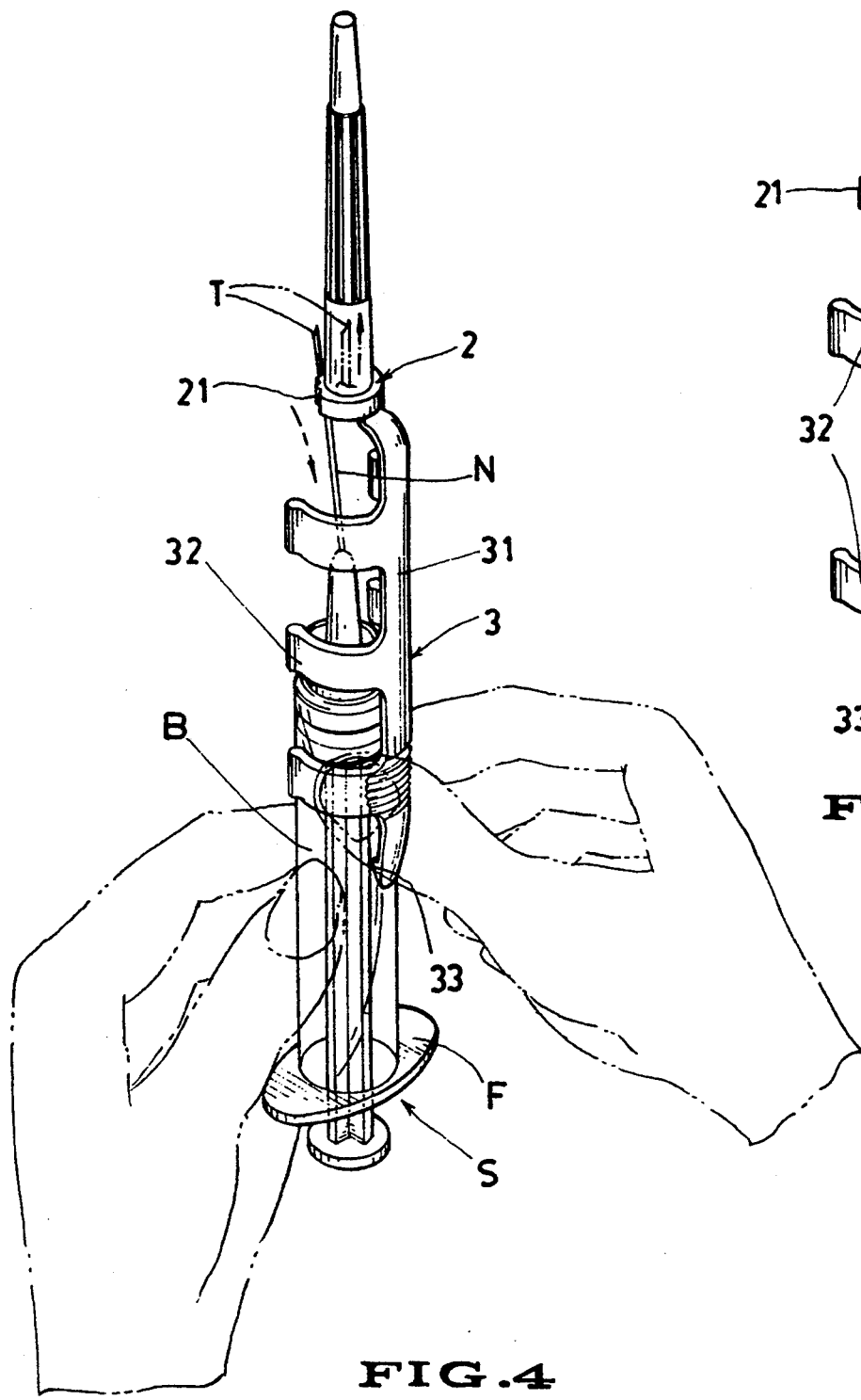
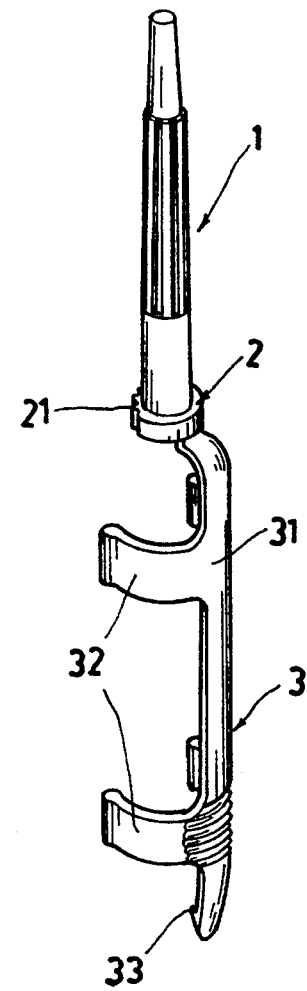
FIG.4
FIG.5

SAFETY SYRINGE SHIELD

BACKGROUND OF THE INVENTION

A conventional syringe shield such as disclosed in U.S. Pat. No. 4,874,383 to McNaughton is provided with a sleeve that can be drawn out over the needle and firmly locked into position on a barrel of the syringe to prevent a user from accidental contact or pricking with the needle.

However, two notches should be recessed in a barrel of the syringe having a front notch for engageably locking the sleeve in position when forwardly drawn to cover the needle, thereby increasing production complexity for making such a syringe structure. Since the syringe after being used will be disposed, the shield of fully cylindrical shape for normally covering the barrel of the syringe completely will cause wasting of plastic material since the shield (16) with big area will be treated for waste disposal.

SUMMARY OF THE INVENTION

The object of the present invention is to provide a safety syringe shield including an elongated closed cap for sealing a syringe needle threin and a cap holder secured to the elongated cap having a pair of holding guide members disposed on two opposite sides of the cap holder for holding the syringe shield to allow the syringe needle to be inserted into the elongated closed cap to prevent accidental contact of the user with the needle.

BRIEF DESCRIPTION OF THE DRAWINGS

FIG. 4 is an illustration showing another inserting operation for putting the needle into the cap of the present invention.

FIG. 5 shows another preferred embodiment of the present invention.

DETAILED DESCRIPTION

Figure 1:
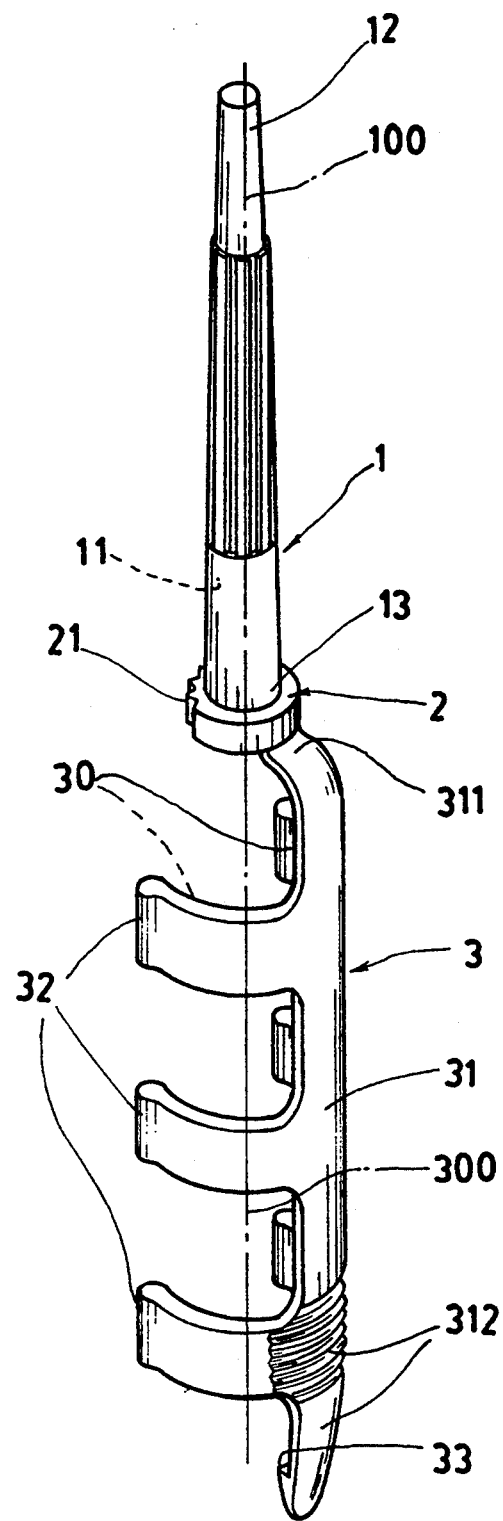
FIG. 1 is a perspective view of the present invention.
Figure 2:
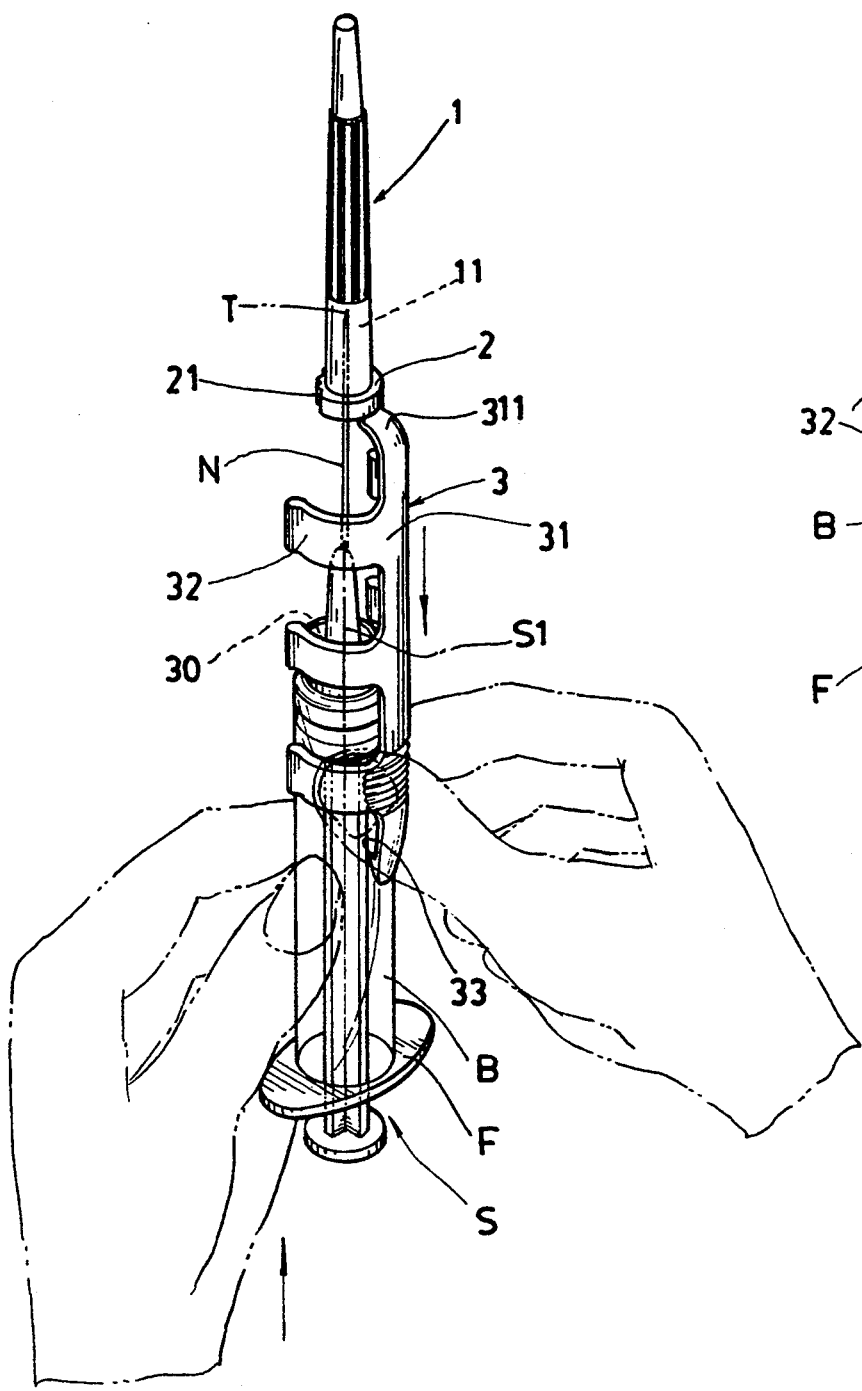
FIG. 2 is an illustration showing an insertion of a syringe needle into a cap of the present invention.
Figure 3:
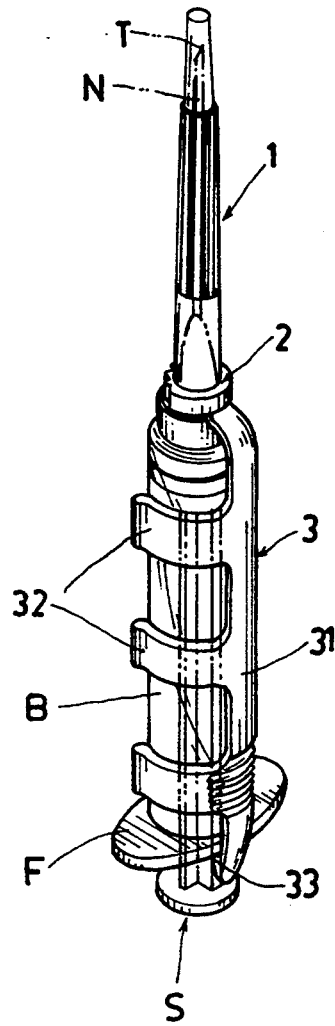
FIG. 3 is an illustration of the present invention after shielding the syringe needle in position.

As shown in FIGS. 1-3, a syringe shield of the present invention comprises: an elongated cap 1, a rim 2 annularly formed on a rear portion of the cap 1, and a holder means 3 secured to the rim 2 of the syringe shield.

The elongated cap 1 is formed as an elongated cylindrical shape tapered forwardly from a rear end portion 13 of the cap towards a front end portion. 12 of the cap 1 with the front end portion 12 closed and having a sleeve interior 11 adapted for inserting a needle N and a needle tip T of a syringe S into the sleeve interior 11 of the cap 1.

The rim 2 is annularly formed on the rear end portion 13 of the elongated cap 1 having a plurality of teeth 21 circumferentially formed oil a periphery of the rim 2 for temporarily engaging a needle N and its tip T on the teeth 21 for preventing sidewardly slipping of the needle N and needle tip T on the rim 2 (as shown in FIG. 4) when trying to insert the needle N into the interior 11 of the cap The syringe shield of this invention may be made of plastic materials.

The holder means 3 attachable to a syringe barrel B includes: a longitudinal stem 31 having a front stem end 311 arcuately bending inwardly and secured to the rim 2 and a rear stem end 312 protruding rearwardly from the stem 31 to form a rear hook member 33 adapted for lockably engaging a flange F formed on a rear portion of a barrel B of the syringe S when inserting the syringe needle N into the cap 1, and at least a pair of holding guide members 32 disposed on two opposite sides of the longitudinal stem 31 for operatively holding and slidably guiding the barrel B of the syringe S for moving the syringe S forwardly in order to insert the needle N and needle tip T into the interior 11 of the cap 1 for safety disposal of a used syringe S without pricking to a person such as a cleaner, a housekeeper, a nurse, a doctor or any others for safety and hygiene reasons.

The holding guide members 32 and the stem 31 should have a total area less than a cylindrical surface area of the barrel B of the syringe S to save cost of the shield since it will be treated as waste disposal.

The stem 31 and each pair of holding guide members 32 are formed with an arcuate groove 30 circumferentially engageable with a cylindrical surface of the barrel B of the syringe S for snugly engaging and sliding of the barrel B in the holder means 3 for smooth insertion of the needle N and needle tip T into the cap 1.

After finishing a medical injection by the needle N of the syringe S, the needle N and the needle tip T of the syringe S is positioned to aim at the interior 11 of the cap 1 when holding the barrel B of the syringe S by a user's left hand as shown in FIG. 2, and the holder means 3 is held by the user's right hand, the syringe S is then pushed forwardly to insert the needle N and the tip T into the interior 11 of the cap 1 for shielding the needle tip T and the rear, hook member 33 is engaged with the flange F at a rear end portion of the barrel to lock the syringe shield of the present invention on the syringe S as shown in FIG. 3 for safety disposal of a used syringe.

If the needle tip T is inclinedly moved when forwardly inserting the needle N into the cap 1 as shown in FIG. 4, the needle tip T and the needle N will be engaged in two neighbouring teeth 21 of the rim 2 to prevent slipping away of the needle 2 sidewardly. A further retraction of the inclined needle tip T to re-aim at the interior 11 of the cap and then the needle N can be re-inserted into the cap 1 for safety disposal.

The number of pairs of holding guide members 32 of the holder means 3 of the present invention may be three pairs as shown in FIG. 1 or may be two pairs as shown in FIG. 5, which are not limited in this invention.

The present invention is superior to a conventional syringe shield with the following advantages:

1. When inserting a used needle N of the syringe S into the cap 1, a holder means 3 is provided to be held by a user's hand, thereby preventing a pricking of the needle to the user.

2. The holding guide members 32 occupy merely a partial area of the syringe barrel B, not fully covering the area of the syringe barrel for saving cost and for enhancing environmental protection on a point of view of waste disposal.

The cap 1 and the holder means 3 of the present invention respectively define a longitudinal cap axis 100 and a longitudinal holder axis 300, operatively aligned with a longitudinal axis S1 of the syringe S and syringe needle N for a smooth insertion of the needle N into the cap 1.

I claim:

1. A safety syringe shield comprising:

an alongated cap adapted for sealing a needle of a syringe therein and having a rim annularly formed on a rear end portion of said elongated cap; and a holder means secured to said elongated cap, and slidably engageable with a syringe barrel and protruding rearwardly from said elongated cap adapted to be held by a user, whereby upon engagement of said syringe barrel in said holder means and upon forwardly pushing of the syringe to insert the needle into said cap, said needle of said syringe will be shielded in said cap for safety disposal;

said rim having plurality of teeth circumferentially formed on a periphery of the rim for temporarily engaging the needle and its tip on the teeth for preventing sidewardly slipping of the needle and needle tip from the rim when inserting the needle into an interior of the cap; and said holder means attachable to a syringe barrel including a longitudinal stem having a front stem end arcuately bending inwardly and secured to the ring and a rear stem end protruding rearwardly from the stem to form a rear hook member adapted for lockably engaging the flange formed on a rear portion of a barrel of the syringe when inserting the needle into the cap, and at least a pair of holding guide members disposed on two opposite sides of the longitudinal stem for operatively holding and slidably guiding the barrel of the syringe for moving the syringe forwardly in order to insert the needle and a needle tip thereof into an interior of the cap for disposal of a used syringe without pricking a person.

2. A safety syringe shield according to claim 1, wherein said stem and each said pair of said holding guide members of said holder means are formed with an arcuate groove circumferentially engageable with a cylindrical surface of the barrel of the syringe for snugly engaging and sliding of the barrel in the holder means for smooth insertion of the needle and needle tip in the cap.

3. A safety syringe shield according to claim 1, wherein said holding guide members and said stem of said holder means have a total surface area less than a cylindrical surface area of the barrel of the syringe.

* * * * *